(12) United States Patent
Carlson et al.

(10) Patent No.: US 7,356,965 B2
(45) Date of Patent: Apr. 15, 2008

(54) MULTI-EMBRYO MANUFACTURED SEED

(75) Inventors: William C. Carlson, Olympia, WA (US); Mollie K. Heilesen, Tacoma, WA (US); Paul G. Gaddis, Seattle, WA (US)

(73) Assignee: Weyerhaeuser Co., Federal Way, WA (US)

( * ) Notice: Subject to any disclaimer, the term of this patent is extended or adjusted under 35 U.S.C. 154(b) by 271 days.

(21) Appl. No.: 10/985,216

(22) Filed: Nov. 9, 2004

(65) Prior Publication Data

US 2005/0132436 A1 Jun. 16, 2005

Related U.S. Application Data

(60) Provisional application No. 60/529,133, filed on Dec. 12, 2003.

(51) Int. Cl.
*A01C 1/94* (2006.01)
*A01H 1/00* (2006.01)
*C12N 15/82* (2006.01)
*C12N 15/87* (2006.01)
*A01N 25/26* (2006.01)

(52) U.S. Cl. .................. 47/56.7; 800/278; 504/100
(58) Field of Classification Search ............... 47/56.7; 800/278; 504/100
See application file for complete search history.

(56) References Cited

U.S. PATENT DOCUMENTS

| | | |
|---|---|---|
| 2,309,702 A | 2/1943 | Kirschenbaum |
| 2,502,809 A | 4/1950 | Vogelsang |
| 2,809,772 A | 10/1957 | Weisz |
| 3,034,905 A | 5/1962 | Weintraub et al. |
| 3,098,320 A | 7/1963 | Estkowski et al. |
| 3,545,129 A | 12/1970 | Schreiber et al. |
| 3,688,437 A | 9/1972 | Hamrin |
| 3,690,034 A | 9/1972 | Knapp |
| 3,734,987 A | 5/1973 | Hamrin |
| 3,850,753 A | 11/1974 | Chibata et al. |
| 4,147,930 A | 4/1979 | Browne et al. |
| 4,166,006 A | 8/1979 | Hertl et al. |
| 4,252,827 A | 2/1981 | Yokoyama et al. |
| 4,465,017 A | 8/1984 | Simmons |
| 4,562,663 A | 1/1986 | Redenbaugh |
| 4,583,320 A | 4/1986 | Redenbaugh |
| 4,615,141 A | 10/1986 | Janick et al. |

(Continued)

FOREIGN PATENT DOCUMENTS

CA 1241552 9/1988

(Continued)

OTHER PUBLICATIONS

Adlercreutz, P., and B. Mattiasson, "Oxygen Supply to Immobilized Biocatalysts. A Model Study," *Acta Chem. Scand.* B36:651-653, 1982.

(Continued)

*Primary Examiner*—Kent L Bell
(74) *Attorney, Agent, or Firm*—Christensen O'Connor Johnson Kindness (57) ABSTRACT

A manufactured seed (20) is provided. The manufactured seed includes a first seed shell (22a) and a first restraint (32a) disposed within the first shell. The first restraint includes a cavity (38a), and at least two embryos (34a) and (34b) disposed within the manufactured seed.

15 Claims, 7 Drawing Sheets

U.S. PATENT DOCUMENTS

| | | | |
|---|---|---|---|
| 4,628,633 | A | 12/1986 | Nilsson |
| 4,665,648 | A | 5/1987 | Branco et al. |
| 4,715,143 | A | 12/1987 | Redenbaugh et al. |
| 4,769,945 | A | 9/1988 | Motoyama et al. |
| 4,777,762 | A | 10/1988 | Redenbaugh et al. |
| 4,777,907 | A | 10/1988 | Sänger |
| 4,779,376 | A | 10/1988 | Redenbaugh |
| 4,780,987 | A | 11/1988 | Nelsen et al. |
| 4,802,305 | A | 2/1989 | Kojimoto et al. |
| 4,802,905 | A | 2/1989 | Spector |
| 4,806,357 | A | 2/1989 | Garrett et al. |
| 4,808,430 | A | 2/1989 | Kouno |
| 4,866,096 | A | 9/1989 | Schweighardt |
| 4,879,839 | A | 11/1989 | Gago et al. |
| 5,010,685 | A | 4/1991 | Sakamoto et al. |
| 5,044,116 | A | 9/1991 | Gago et al. |
| 5,181,259 | A | 1/1993 | Rorvig |
| 5,183,757 | A | 2/1993 | Roberts |
| 5,236,469 | A | 8/1993 | Carlson et al. |
| 5,250,082 | A | 10/1993 | Teng et al. |
| 5,258,132 | A | 11/1993 | Kamel et al. |
| 5,284,765 | A | 2/1994 | Bryan et al. |
| 5,427,593 | A | 6/1995 | Carlson et al. |
| 5,451,241 | A | 9/1995 | Cartson et al. |
| 5,464,769 | A | 11/1995 | Attree et al. |
| 5,529,597 | A | 6/1996 | Iijima |
| 5,564,224 | A | 10/1996 | Carlson et al. |
| 5,565,355 | A | 10/1996 | Smith |
| 5,666,762 | A | 9/1997 | Carlson et al. |
| 5,680,320 | A | 10/1997 | Helmer et al. |
| 5,687,504 | A | 11/1997 | Carlson et al. |
| 5,701,699 | A | 12/1997 | Carlson et al. |
| 5,732,505 | A | 3/1998 | Carlson et al. |
| 5,771,632 | A | 6/1998 | Liu et al. |
| 5,784,162 | A | 7/1998 | Carib et al. |
| 5,799,439 | A | 9/1998 | MacGregor |
| 5,821,126 | A | 10/1998 | Durzan et al. |
| 5,842,150 | A | 11/1998 | Renberg et al. |
| 5,877,850 | A | 3/1999 | Ogata |
| 5,930,803 | A | 7/1999 | Becker et al. |
| 5,960,435 | A | 9/1999 | Rathmann et al. |
| 6,021,220 | A | 2/2000 | Anderholm |
| 6,092,059 | A | 7/2000 | Straforini et al. |
| 6,119,395 | A | 9/2000 | Hartle et al. |
| 6,145,247 | A | 11/2000 | McKinnis |
| 6,470,623 | B1 * | 10/2002 | Hirahara ..................... 47/57.6 |
| 6,567,538 | B1 | 5/2003 | Pelletier |
| 6,582,159 | B2 | 6/2003 | McKinnis |
| 2002/0192686 | A1 | 12/2002 | Adorjan et al. |
| 2003/0055615 | A1 | 3/2003 | Zhang et al. |

FOREIGN PATENT DOCUMENTS

| | | |
|---|---|---|
| CA | 1250296 | 2/1989 |
| EP | 0 107 141 A1 | 5/1984 |
| EP | 0 300 730 A1 | 1/1989 |
| EP | 0 380 692 A1 | 8/1990 |
| EP | 0776601 A1 | 6/1997 |
| FR | 2 680 951 A1 | 3/1993 |
| JP | 61040708 | 2/1986 |
| JP | 62275604 | 11/1987 |
| JP | 63133904 | 6/1988 |
| JP | 63152905 | 6/1988 |
| JP | 2-46240 | 2/1990 |
| JP | 407179683 A | 7/1995 |
| WO | WO 91/00781 A1 | 1/1991 |
| WO | WO 91/01803 | 2/1991 |
| WO | WO 92/07457 A1 | 5/1992 |
| WO | WO 95/05064 | 2/1995 |
| WO | WO 98/33375 | 8/1998 |
| WO | WO 99/26470 | 6/1999 |

OTHER PUBLICATIONS

Adlercreutz, P., and B. Mattiasson, "Oxygen Supply to Immobilized Cells: 1. Oxygen Production by Immobilized *Chlorella pyrenoidosa,*" *Enzyme Microbial Technol.* 4:332-336, 1982.

Adlercreutz, P., and B. Mattiasson, "Oxygen Supply to Immobilized Cells. 3. Oxygen Supply by Hemoglobin or Emulsions of Perfluorochemicals," *Eur. J. Appl. Microbiol. & Biotechnol.* 16:165-170, 1982.

Bapat, V.A., "Studies on Synthetic Seeds of Sandalwood (*Santalum album L.*) and Mulberry (*Morus indica L.*)," K. Redenbaugh (ed.), *Synseeds: Applications of Synthetic Seeds to Crop Improvement,* CRC Press, Inc., Boca Raton, Fla., 1993, pp. 381-407.

Bapat, V.A., and P.S. Rao, "In Vivo Growth of Encapsulated Axillary Buds of Mulberry (*Morus indica L.*)," *Plant Cell, Tissue and Organ Culture* 20:69-70, 1990.

Bapat, V.A., and P.S. Rao, "Sandalwood Plantlets from 'Synthetic Seeds,'" *Plant Cell Reports* 7:434-436, 1988.

Buchenauer, H., "Mode of Action and Selectivity of Fungicides Which Interfere with Ergosterol Biosynthesis," *Proceedings of the 1977 British Crop Protection Conference—Pests and Diseases,* Brighton, U.K., 1977, pp. 699-711.

Chandler, D., et al., "Effects of Emulsified Perfluorochemicals on Growth and Ultrastructure of Microbial Cells in Culture," *Biotechnol. Letters* 9(3):195-200, 1987.

Cheng, Z., and P.P. Ling, "Machine Vision Techniques for Somatic Coffee Embryo Morphological Feature Extraction," *American Society of Agricultural Engineers* 37(5):1663-1669, 1994.

Chi, C.-M., et al., "An Advanced Image Analysis System for Evaluation of Somatic Embryo Development," *Biotechnology and Bioengineering* 50:65-72, Apr. 1996.

Clark, Jr., L.C., et al., "Emulsions of Perfluoronated Solvents for Intravascular Gas Transport," *Fed. Proceed.* 34(6):1468-1477, 1975.

Clark, Jr., L.C., et al., "The Physiology of Synthetic Blood," *J.Thorac. & Cardiovasc. Surg.* 60(6):757-773, 1970.

Damiano, D., and S.S. Wang, "Novel Use of Perfluorocarbon for Supplying Oxygen to Aerobic Submerged Cultures," *Biotechnol. Letters* 7(2):81-86, 1985.

Datta, S.K., and I. Potrykus, "Artifical Seeds in Barley: Encapsulation of Microspore-Derived Embryos," *Thero. Appl. Genet.* 77:820-824, 1989.

Dumet, D., et al., "Cryopreservation of Oil Palm (*Elaeis guincesis Jacq.*) Somatic Embryos Involving A Desiccation Step," *Plant Cell Reports* 12:352-355, 1993.

Dupuis, J.-M., et al., "Pharmaceutical Capsules as a Coating System for Artificial Seeds," *Bio/Technol.* 12:385-389, 1994.

Ebert, W.W., and P.F. Knowles, "Inheritance of Pericarp Types, Sterility, and Dwarfness in Several Safflower Crosses," *Crop Science* 6:579-582, 1966.

Fujii, A., et al., "Artificial Seeds for Plant Propagation," *Trends in Bio/Technol.* 5:335-339, 1987.

Fujii, J., et al., "ABA Maturation and Starch Accumulation in Alfalfa Somatic Embryos" (Abstract), In Vitro 25 (3, Part 2):61A, 1989.

Fujii, J., et al., "Improving Plantlet Growth and Vigor From Alfalfa Artificial Seed" (Abstract), In Vitro 24 (3, Part 2):70A, 1989.

Fujita, T., et al., "Fluorocarbon Emulsion as a Candidate for Artificial Blood," *Europ. Surg. Res.* 3:436-453, 1971.

Geyer, R.P., "'Bloodless' Rats Through the Use of Artificial Blood Substitutes," *Fed. Proceed* 34(6):1499-1505, 1975.

Gray, D.J., and A. Purohit, "Somatic Embryogenesis and Development of Synthetic Seed Technology," *Crit. Rev. Plant Sci.* 10(1):33-61, 1991.

Grob, J.A., et al., "Dimensional Model of Zygotic Douglas-Fir Embryo Development," *International Journal of Plant Sciences* 160(4):653-662, 1999.

Gupta, P.K., and D.J. Durzan, "Biotechnology of Somatic Polyembryogenesis and Plantlet Regeneration in Loblolly Pine," *Bio/Technol.* 5:147-151, 1987.

Ibarbia, E.A., "Synthetic Seed: Is It the Future," *Western Grower and Shipper* 59:12, 1988.

Janick, J., "Production of Synthetic Seed via Desiccation and Encapsulation" (Abstract), In Vitro 24 (3, Part 2):70A, 1989.

Kamada, H., et al., "New Methods for Somatic Embryo Induction and Their Use of Synthetic Production" (Abstract), In Vitro 24(3, Part 2):71A, 1988.

Kim YH, "ABA and Polyox-Encapsulation or High Humidity Increases Survival of Desiccated Somatic Embryos of Celery," *HortScience* 24(4):674-676, 1989.

King, A.T., et al., "Perfluorochemicals and Cell Culture," *Biotechnol.* 7:1037-1042, 1989.

Kitto, S.L., and J. Janick, "A Citrus Embryo Assay to Screen Water-Soluble Resins as Synthetic Seed Coats," *HortScience* 20(1):98-100, 1985.

Kitto, S.L., and J. Janick, "Production of Synthetic Seeds by Encapsulating Asexual Embryos of Carrot," *J. Amer. Soc. Hort. Sci.* 110(2):277-282, 1985.

Li, X.-Q., "Somatic Embryogenesis and Synthetic Seed Technology Using Carrot as a Model System," in K. Redenbaugh (ed.), *Synseeds: Applications of Synthetic Seeds to Crop Improvement*, CRC Press, Inc., Boca Raton, Fla., 1993, pp. 289-304.

Mattiasson, B., and P. Adlercreutz, "Use of Perfluorochemicals for Oxygen Supply to Immobilized Cells," *Ann. N.Y. Acad. Sci.* 413:545-547, 1984.

Paulet, F., et al., "Cryopreservation of Apices of In Vitro Plantlets of Sugarcane (*Saccharum* sp. Hybrids) Using Encapsulation/Dehydration," *Plant Cell Reports* 12:525-529, 1993.

Redenbaugh, K., et al., "Encapsulated Plant Embryos," *Biotechnology in Agriculture*, 1988, pp. 225-248.

Redenbaugh, K., et al., "Encapsulation of Somatic Embryos for Artificial Seed Production" (Abstract), In Vitro 20(2):256-257, 1984.

Redenbaugh, K., et al., "Encapsulation of Somatic Embryos in Synthetic Seed Coats," *HortScience* 22(5):803-809, 1987.

Redenbaugh, K., et al., "III.3 Artificial Seeds—Encapsulated Somatic Embryos," *Biotech. in Agr. & For.* 17:395-416, 1991.

Redenbaugh, K., et al., "Scale-Up: Artificial Seeds," in Green et al. (eds.), *Plant Tissue and Cell Culture*, Alan R. Liss, Inc., New York, 1987, pp. 473-493.

Redenbaugh, K., et al., "Somatic Seeds: Encapsulation of Asexual Plant Embryos," *Bio/Technology* 4:797-801, 1986.

Riess, J.G., and M. Le Blanc, "Perfluoro Compounds as Blood Substitutes," *Angew. Chem. Int. Ed. Engl.* 17(9):621-634, 1978.

Rogers, M., "Synthetic-Seed Technology," *Newsweek*, Nov. 28, 1983.

Sanada, M., et al., "Celery and Lettuce," in M.K. Redenbaugh (ed.), *Synseeds: Applications of Synthetic Seeds to Crop Improvement*, CRC Press, Inc., Boca Raton, Fla., 1993, pp. 305-322.

Senaratna, T., "Artificial Seeds," *Biotech Adv.* 10(3)379-392, 1992.

Sharma SK et al., "Novel Compositions of Emulsified Perfluorocarbons for Biological Applications," *Brit. J. Pharmacol.* 89:665P, 1986.

Stuart, D.A., and M.K. Redenbaugh, "Use of Somatic Embryogenesis for the Regeneration of Plants," in H.M. LeBaron et al. (eds.), *Biotechnology in Agricultural Chemistry*, American Chemical Society, Washington, D.C., 1987, pp. 87-96.

Teasdale, R.D., and P.A. Buxton, "Culture of *Pinus radiata* Embryos With Reference to Artificial Seed Production," *New Zealand J. For. Sci.* 16(3):387-391, 1986.

Tessereau, H. et al., "Cryopreservation of Somatic Embryos: A Tool for Germplasm Storage and Commercial Delivery of Selected Plants," *Ann. Bot.* 74:547-555, 1994.

Timmis, R., "Bioprocessing for Tree Production in the Forest Industry: Conifer Somatic Embryogenesis," *Biotechnology Progress* 14(1):156-166, 1998.

Weyerhaeauser, G.H., "Biotechnology in Forestry: The Promise and the Economic Reality" *Solutions! for People, Processes and Paper* 86(10):28-30, Oct. 2003.

\* cited by examiner

MULTI-EMBRYO MANUFACTURED SEED

CROSS REFERENCE TO RELATED APPLICATION

The present application claims the benefit of U.S. Provisional Application No. 60/529,133, filed Dec. 12, 2003.

FIELD OF THE INVENTION

The present invention relates generally to artificial seeds and, more particularly, to multi-embryo manufactured seeds.

BACKGROUND OF THE INVENTION

Asexual propagation of plants has been shown for some species to yield large numbers of genetically identical embryos, each having a capacity to develop into a normal plant. Such embryos are usually further cultured under laboratory conditions until they reach an autotrophic "seedling" state characterized by an ability to produce its own food via photosynthesis, resist desiccation, produce roots able to penetrate soil, and fend off soil microorganisms. Some researchers have experimented with the production of artificial seeds, known as manufactured seeds, in which individual plant somatic or zygotic embryos are encapsulated in a seed coat. Examples of such manufactured seeds are disclosed in U.S. Pat. No. 5,701,699, issued to Carlson et al., the disclosure of which is hereby expressly incorporated by reference.

Typical manufactured seeds include a seed shell, synthetic gametophyte and a plant embryo. A manufactured seed that does not include the plant embryo is known in the art as a "seed blank." The seed blank typically is a cylindrical capsule having a closed end and an open end. The synthetic gametophyte is placed within the seed shell to substantially fill the interior of the seed shell. A longitudinally extending hard porous insert, known as a cotyledon restraint, may be centrally located within one end of the seed shell, surrounded by the synthetic gametophyte, and includes a centrally located cavity extending partially through the length of the cotyledon restraint.

The cavity is sized to receive the plant embryo therein. The well-known plant embryo includes a radicle end and a cotyledon end. The plant embryo is deposited within the cavity of the cotyledon restraint, cotyledon end first. The plant embryo is then sealed within the seed blank by at least one end seal. There is a weakened spot in the end seal to allow the radicle end of the plant embryo to penetrate the end seal.

After a relatively large number of manufactured seeds are assembled, they are sowed in a nursery bed. As such, they are allowed to germinate with the anticipation of yielding a large number of healthy seedlings having desired characteristics. Although currently available manufactured seeds are relatively successful in yielding a reasonable number of healthy seedlings, such manufactured seeds are not without problems.

As an example, research has shown that embryo quality can reduce the germination of manufactured seeds. As a non-limiting example, with one set of embryos, germination was 50%. This can be improved by various sorting methods. As a result, as measured against the successful yield rate, the cost of manufactured seeds with low quality embryos is proportionately higher when evaluated against crop yield.

Thus, there exists a need for a multi-embryo manufactured seed that produces a higher successful yield rate than those currently available in the art.

SUMMARY OF VARIOUS EMBODIMENTS OF THE INVENTION

A manufactured seed is provided. The manufactured seed includes a first seed shell and a first restraint disposed within the first seed shell. The manufactured seed also includes at least two embryos disposed within the manufactured seed. In another embodiment of the present invention, the manufactured seed also includes a second seed shell coupled to the first seed shell, and includes a second restraint having a cavity. In this embodiment, one of the at least two embryos is disposed within the cavity of the first restraint and another of the least two embryos is disposed within the cavity of the second restraint.

In yet another embodiment of the present invention, the first and second seed shells are coaxially aligned. In still yet another embodiment, the manufactured seed includes a plurality of restraints disposed in one end of the first seed shell.

A multi-embryo manufactured seed formed in accordance with various embodiments of the present invention has several advantages over currently available manufactured seeds. Because the multi-embryo manufactured seed of the present invention includes at least two embryos, there is a greater chance of producing a manufactured seed yielding an acceptable successful seedling rate per manufactured seed. Further, because multiple embryos are disposed in each manufactured seed, the need to evaluate and segregate qualified embryos from unqualified embryos prior to insertion into the manufactured seed is reduced. This results in a more cost effective manufactured seed as a time consuming step in the manufactured seed assembly is eliminated.

Thus, a multi-embryo manufactured seed formed in accordance with the various embodiments of the present invention has a high degree of reliability, and is capable of mass production at a relatively low cost.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
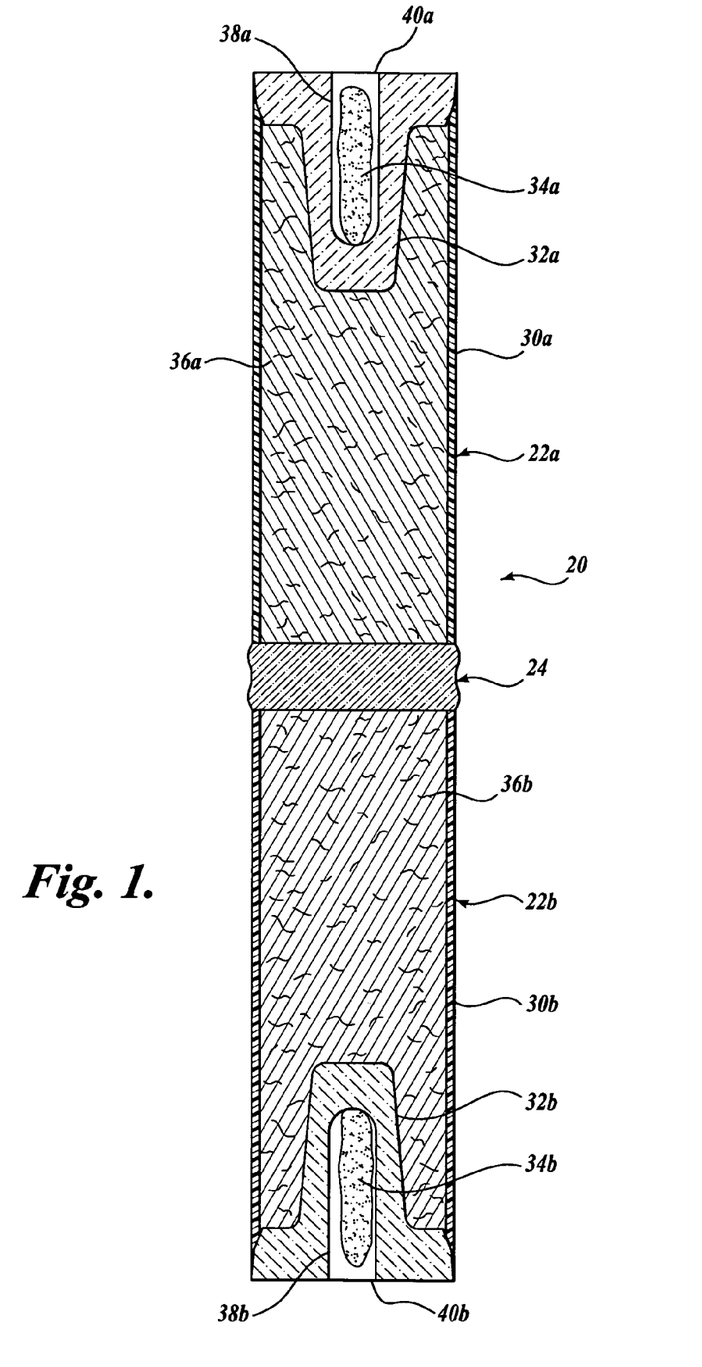
FIG. 1 is a cross-sectional side view of a multi-embryo manufactured seed formed in accordance with one embodiment of the present invention, showing two manufactured seed blanks coaxially joined at one end by a bonding material.

FIG. 1 illustrates a multi-embryo manufactured seed (hereinafter referred to as "manufactured seed 20") constructed in accordance with one embodiment of the present invention. The manufactured seed 20 includes first and second seeds 22a and 22b, and a bond portion 24. As both the first and second seeds 22a and 22b are identically configured, only one seed 22a will be described in greater detail. Therefore, the description of the first seed 22a is equally applicable to the second seed 22b.

The first seed 22a includes a seed shell 30a, a cotyledon restraint 32a, and an embryo 34a. The interior of the seed shell 30a is filled with a nutritive media 36a. Such a seed 22a is disclosed in U.S. Pat. No. 5,701,699, issued to Carlson et al., the disclosure of which is hereby expressly incorporated by reference.

The seed shell 30a is suitably formed from a tubular material, such as a straw of fibrous material, and is sectioned in appropriate lengths. The cotyledon restraint 32a is suitably manufactured from a hard, porous material, such as ceramic, and includes a longitudinally extending cavity 38a. The cavity 38a extends partially through one end of the cotyledon restraint 32b and includes an open end known as a cotyledon restraint opening 40a. The cavity 38a is sized to receive the plant embryo 34a therein.

Still referring to FIG. 1, the bond portion 24 will now be described in greater detail. The bond portion 24 is suitably formed from a wax and extends between two opposed ends of the first and second seeds 22a and 22b. Although wax is the preferred material to form the bond portion, other types of materials, such as glue, are also within the scope of the present invention. Further, in other embodiments, the bond portion 24 is accomplished by ablation by a laser, or a sleeve, as will be described in greater detail below.

As assembled, the manufactured seed 20 is then distributed in a nursery bed where the embryos 34a and 34b are permitted to germinate. In some circumstances, both embryos 34a and 34b are healthy embryos and each germinates to yield an acceptable seedling. However, in other circumstances, only one of the two embryos 34a and 34b successfully germinate to produce a desirable seedling.

Figure 2:
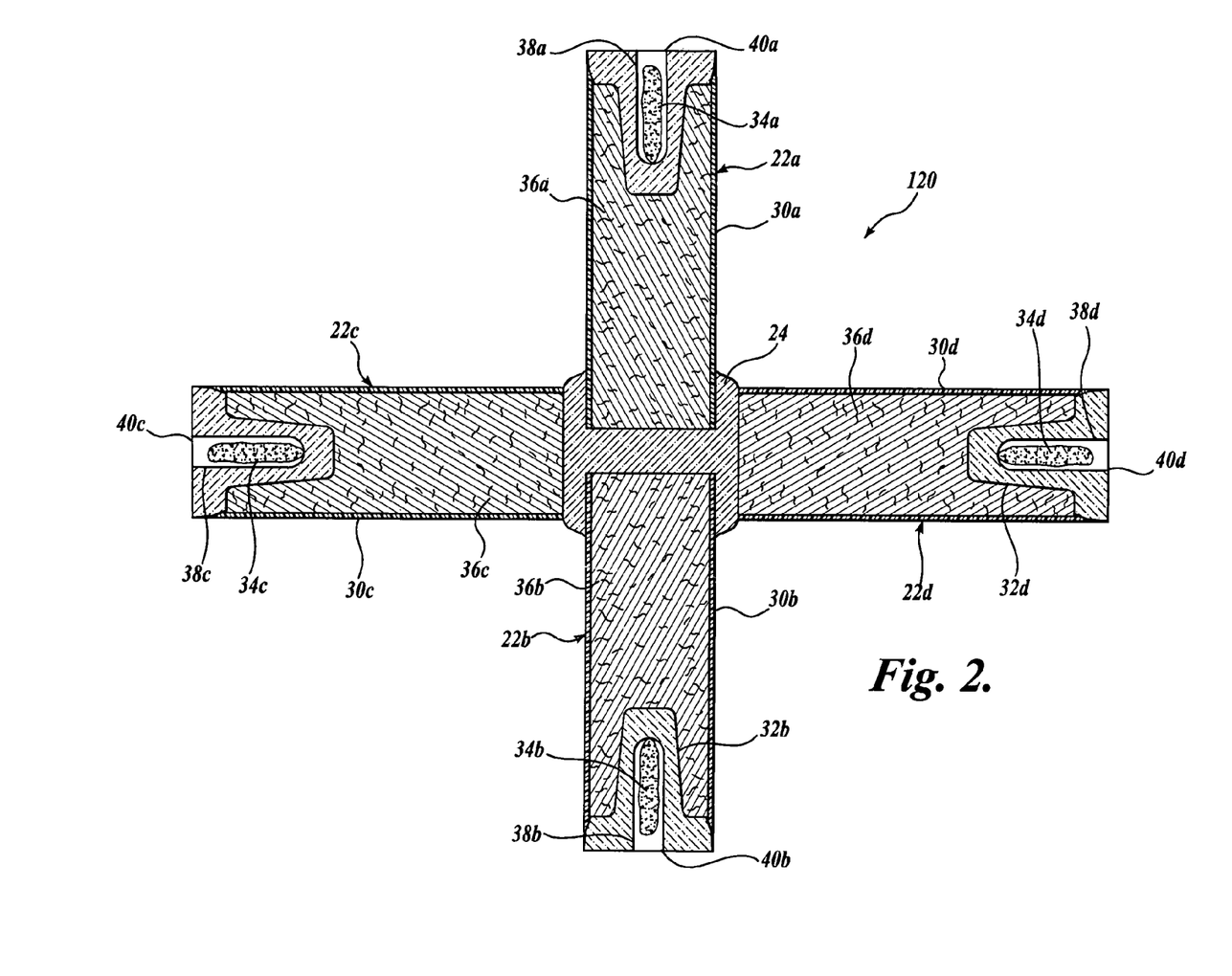
FIG. 2 is a cross-sectional side view of a multi-embryo manufactured seed formed in accordance with another embodiment of the present invention, showing four manufactured seed blanks co-joined at one end by a bonding material.

Referring now to FIG. 2, a manufactured seed 120, formed in accordance with another embodiment of the present, invention will now be described in greater detail. The manufactured seed 120 of the present embodiment is identical in materials and use as the previously described embodiment with reference to FIG. 1, with the exception that the manufactured seed 120 includes a third and fourth seed 22c and 22d. In this embodiment, all four seeds 22a-22d have one end thereof connected by the bond portion 24, such that the manufactured seed 120 is substantially cross-shaped, or X-shaped, in configuration. Although a total of four manufactured seeds are illustrated as sharing a common bond portion, it should be apparent that other embodiments, such as a manufactured seed that includes more or less seeds coupled thereto. As an example, a manufactured seed that includes only three seeds, or one that includes five or six seeds are also within the scope of the present invention.

Figure 3:
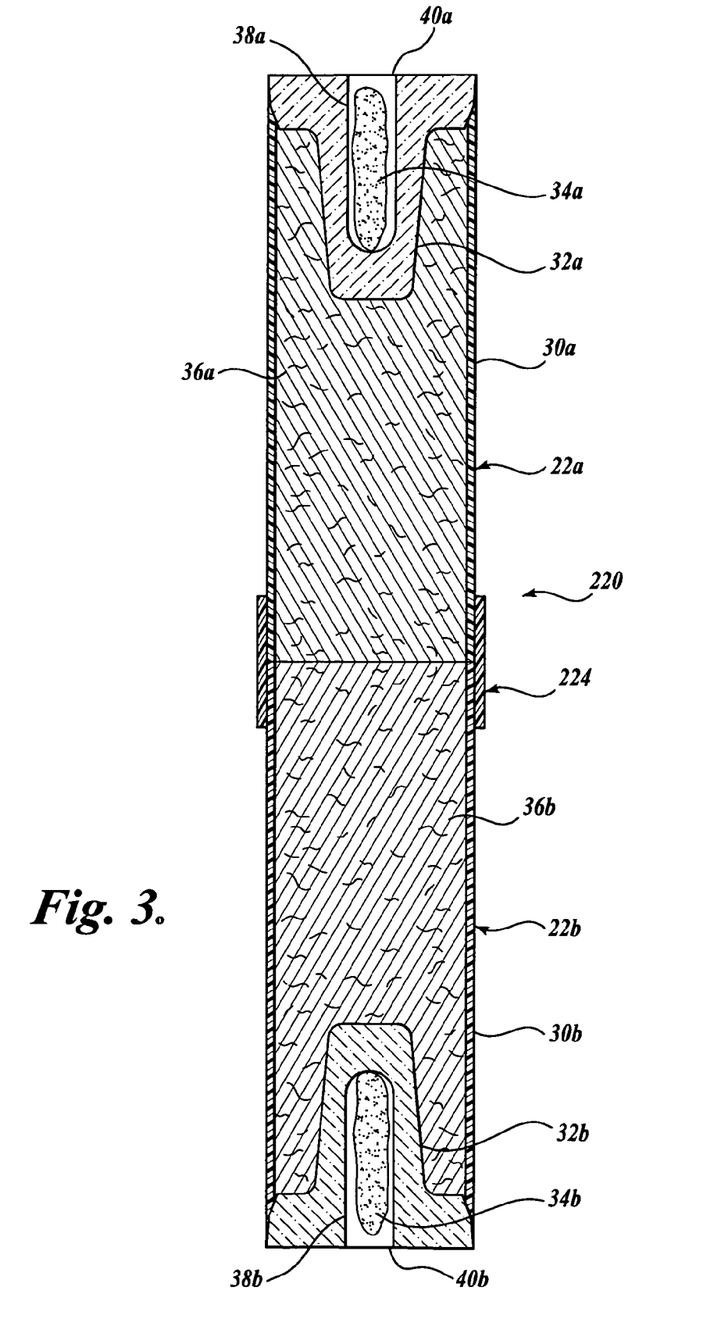
FIG. 3 is a cross-sectional side view of a multi-embryo manufactured seed formed in accordance with another embodiment of the present invention, showing two manufactured seed blanks co-joined at one end by a sleeve.

Referring now to FIG. 3, a manufactured seed 220 formed in accordance with yet another embodiment of the present invention will now be described in greater detail. The manufactured seed 220 is identical in both materials and use for the embodiment described above with respect to FIG. 1, with the exception that the first and second seeds 22a and 22b are coupled together by a sleeve 224. The sleeve 224 is suitably any material capable of either fusing, melting or otherwise connecting opposed ends of the first and second seeds 22a and 22b together. As an example, the sleeve 224 is a band of elastic material tightly disposed around the exterior of the first and second seeds 22a and 22b. Other types of materials for the bond portion 224, such as paper, wax impregnated paper, plastic, biodegradable plastic, shrink tubing, rubber tubing, and a glue, are also within the scope of the present invention.

Figure 4:
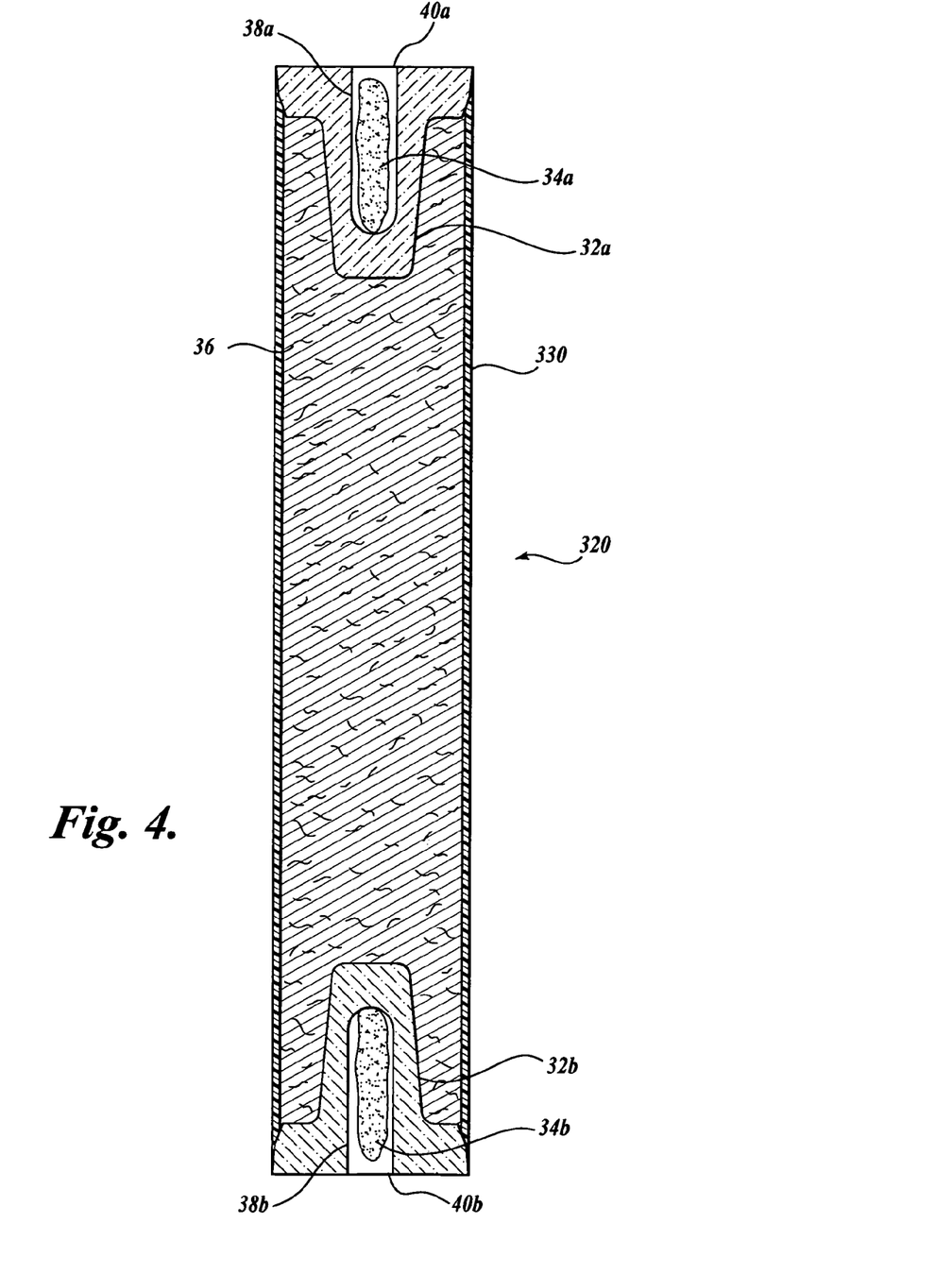
FIG. 4 is a cross-sectional side view of a multi-embryo manufactured seed formed in accordance with still yet another embodiment of the present invention, showing a single seed coat having two restraints disposed in opposite ends of the seed coat.

A manufactured seed 320 formed in accordance with another embodiment of the present invention may be best understood by referring to FIG. 4. The manufactured seed 320 is identical in materials and use to the manufactured seeds described above, with the exception that the manufactured seed 320 includes a single seed shell 330. The cotyledon restraints 32a and 32b are disposed within opposite ends of the seed shell 330, thereby forming a continuous tubular structure.

Figure 5:
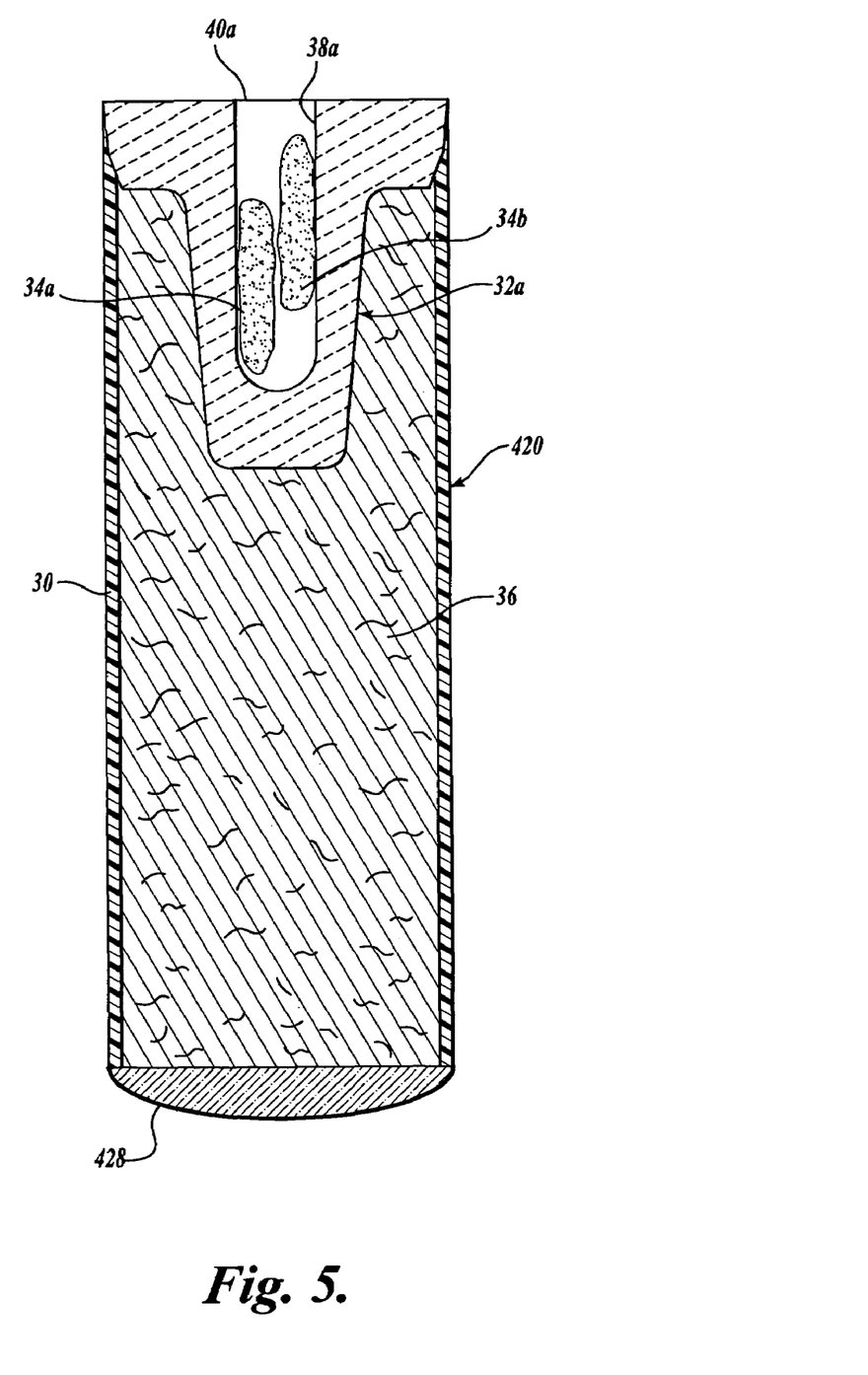
FIG. 5 is a cross-sectional side view of a multi-embryo manufactured seed coat formed in accordance with another embodiment of the present invention, showing two embryos disposed within a manufactured seed having a single restraint.

Referring next to FIG. 5, a manufactured seed 420 formed in accordance with another embodiment of the present invention will now be described in greater detail. The manufactured seed 420 is identical in materials and use as the previous embodiments described above, with the following exception. In that regard, the manufactured seed 420 includes only one cotyledon restraint 32a housing two embryos 34a and 34b within the cavity 38a. Although only two embryos are illustrated, the invention is not intended to be so limited. In that regard, the cotyledon restraint opening 38a may include more embryos, such as three or more, and therefore, such embodiments are also within the scope of the present invention. The manufactured seed 420 also includes a well known dead end seal 428.

Figure 6:
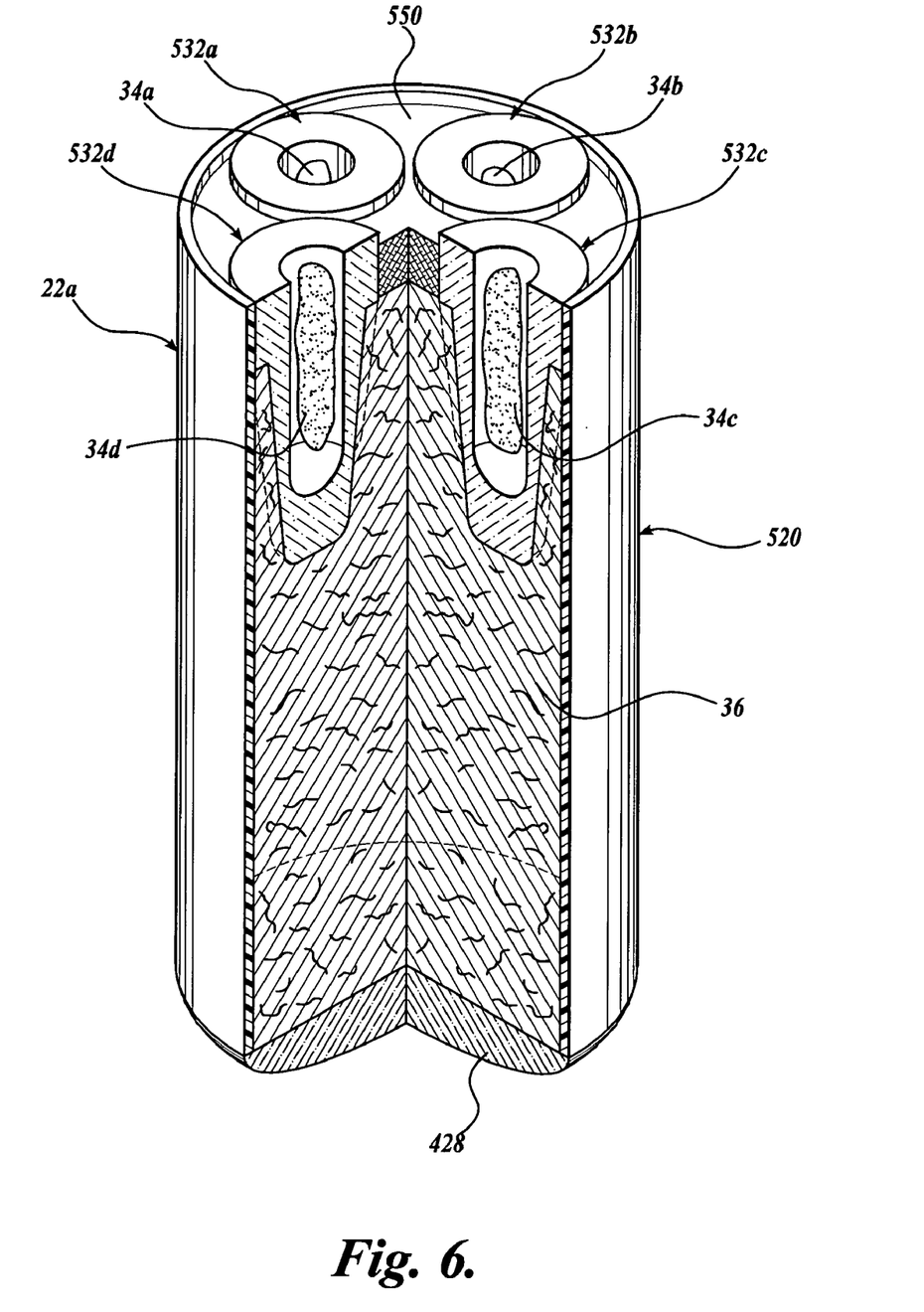
FIG. 6 is a partial cross-section isometric view of a multi-embryo manufactured seed formed in accordance with another embodiment of the present invention, showing a plurality of restraints disposed in one end of the manufactured seed.

A manufactured seed 520 formed in accordance with still yet another embodiment of the present invention may be best understood by referring to FIG. 6. The manufactured seed 520 is identical in materials and use to the previously described embodiments, with the following exceptions. First, the manufactured seed 520 includes a plurality of cotyledon restraints 532a-532d disposed within one end of the seed shell 22a. Another difference between the manufactured seed 520 of the present embodiment and the previously described embodiments is that the cotyledon restraint 532a-532d are seated within the one end of the seed shell 22a by a well known live end seal 550. Such a live end seal 550 is suitably formed from a wax or wax compound. If a thermoplastic material is utilized for the seed shell 22a, the thermoplastic material may be utilized as the "glue" to hold the restraint to the seed shell.

Although the present embodiment is described as containing only four cotyledon restraints, it should be apparent that other embodiments are also within the scope of the present invention. As an example, such a manufactured seed may include two, three, five, or any other combination of cotyledon restraints within the one end of the seed shell 22a. As another example, multiple cotyledon restraints may be disposed in both ends of the seed shell 22*a*, such that a plurality of embryos are disposed in both ends of the seed shell 22*a*. Accordingly, such embodiments are also within the scope of the present invention.

Figure 7:
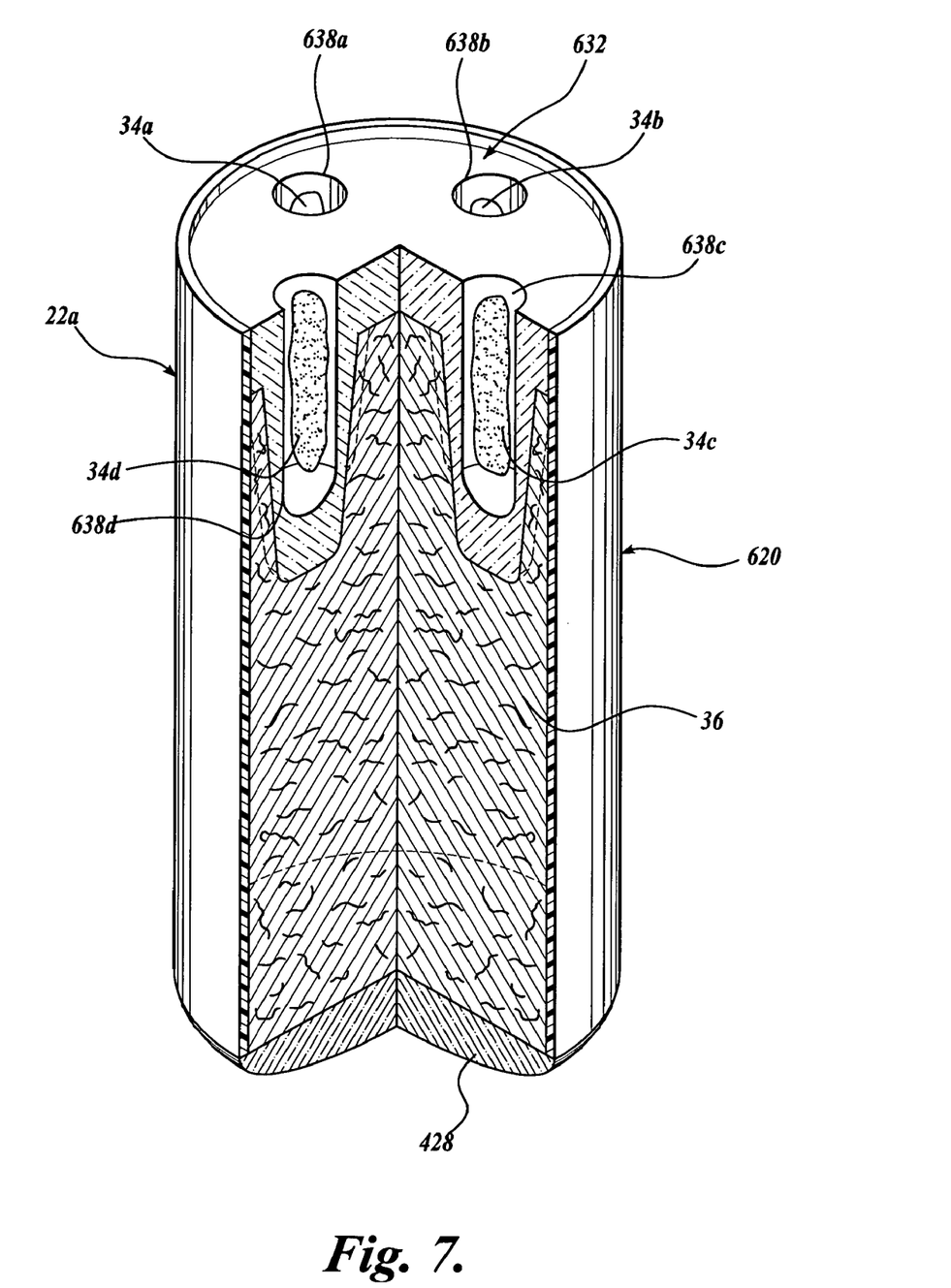
FIG. 7 is a partial cross-section isometric view of a multi-embryo manufactured seed formed in accordance with another embodiment of the present invention, showing a single restraint having a plurality of cavities sized to receive an embryo.

As may be best seen by referring to FIG. 7, a manufactured seed 620 formed in accordance with another embodiment of the present invention will now be described in greater detail. The manufactured seed 620 is identical in materials and use to the previously described embodiment of FIG. 6, with the exception that the manufactured seed 620 includes a single cotyledon restraint 632 having a plurality of cavities 638*a*-638*d*. The cotyledon restraint 632 is suitably disposed within one end of the seed shell 22*a* and is sealed therein by a wax, glue, or thermal plastic melt bond. After an embryo 34*a*-34*d* is disposed within a corresponding cavity, it may be sealed therein by an appropriate and well known live end seal.

It should be apparent that although a cotyledon restraint 632 with a total of four cavities 638*a*-638*d*, is illustrated and described, other cotyledon restraints, such as a cotyledon restraint with two, three, five, six, or more cavities, are also within the scope of the present invention. It should also be apparent that the manufactured seed may include two identically configured, single restraints having a plurality of cavities inserted into both ends of the seed coat. As yet another embodiment, a manufactured seed having, in one end, a single restraint with a plurality of cavities, and a plurality of restraints disposed in the other end of the seed coat. Accordingly, such embodiments are also within the scope of the present invention.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A manufactured seed, comprising:
   (a) a first seed shell;
   (b) a first restraint disposed within the first seed shell, the first restraint having a cavity;
   (c) at least two embryos disposed within the manufactured seed; and
   (d) a second seed shell coupled to the first seed shell, the second seed shell includes a second restraint having a cavity, wherein one of the at least two embryos is disposed within the cavity of the first restraint and a different one of the at least two embryos is disposed within the cavity of the second restraint.

2. The manufactured seed of claim 1, wherein the first and second seed shells are co-axially aligned.

3. The manufactured seed of claim 1, wherein the first and second seed shells are bonded together.

4. The manufactured seed of claim 1, further comprising third and fourth seed shells coupled to the first and second seed shells, the third and fourth seed shells each having a restraint and cavity.

5. A manufactured seed, comprising:
   (a) a seed shell having at least one restraint disposed within the seed shell;
   (b) at least two embryos disposed within the manufactured seed; and
   (c) a second restraint disposed within the seed shell.

6. The manufactured seed of claim 5, wherein the first and second restraints are disposed in opposite ends of the seed shell.

7. A manufactured seed, comprising:
   (a) a seed shell having at least one restraint disposed within the seed shell;
   (b) at least two embryos disposed within the manufactured seed; and
   (c) a second seed shell having a restraint disposed therein, the second seed shell bonded to the seed shell.

8. The manufactured seed of claim 7, wherein both seed shells are coaxially aligned and bonded such that the restraints of the first and second seed shells are disposed at opposite ends of the manufactured seed.

9. The manufactured seed of claim 8, wherein the seed shells are bonded by a wax.

10. A manufactured seed, comprising:
    (a) a seed shell having at least one restraint disposed within the seed shell, wherein the at least one restraint includes a plurality of cavities; and
    (b) at least two embryos disposed within the manufactured seed.

11. The manufactured seed of claim 10, wherein each one of the plurality of cavities is sized to receive at least one of the at least two embryos.

12. A manufactured seed, comprising:
    (a) a seed shell,
    (b) means for restraining at least two embryos within the manufactured seed; and
    (c) a second seed shell in communication with the seed shell.

13. The manufactured seed of claim 12, further comprising a second means for restraining at least one of the at least two embryos, the second means for restraining being disposed within the second seed shell.

14. A manufactured seed, comprising:
    (a) a first seed shell;
    (b) a first restraint disposed within the first seed shell, the first restraint having a cavity;
    (c) at least two embryos disposed within the manufactured seed; and
    (d) a second restraint having a cavity, the first and second restraints being disposed within opposite ends of the first seed shell.

15. A manufactured seed, comprising:
    (a) a seed shell having at least one restraint disposed within the seed shell;
    (b) at least two embryos disposed within the manufactured seed; and
    (c) a plurality of seed shells coupled together in a substantially cross-shaped configuration.

* * * * *